(12) United States Patent
Ahn

(10) Patent No.: US 7,321,832 B2
(45) Date of Patent: Jan. 22, 2008

(54) METHOD OF DESIGNING PROBE FROM POLYNUCLEOTIDE GROUP COMPRISING PLURALITY OF POLYNUCLEOTIDES

(75) Inventor: Tae-jin Ahn, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/259,730

(22) Filed: Oct. 26, 2005

(65) Prior Publication Data

US 2006/0110757 A1    May 25, 2006

(30) Foreign Application Priority Data

Oct. 26, 2004   (KR) .................. 10-2004-0085798

(51) Int. Cl.
  *G01N 33/48*   (2006.01)
  *C12Q 1/68*    (2006.01)
  *C07H 21/00*   (2006.01)

(52) U.S. Cl. ........................... 702/19; 435/6; 536/25.3

(58) Field of Classification Search .................... None
See application file for complete search history.

(56) References Cited

U.S. PATENT DOCUMENTS 5,556,749 A    9/1996  Mitsuhashi et al.

2003/0054346 A1   3/2003  Shannon et al.
2004/0157254 A1   8/2004  Kwon

OTHER PUBLICATIONS

Extended European Search Report for European Application No. 05023049.9-2201.
Meier, H. et al., "Development and implementation of a parallel algorithm for the fast design of oligonucleotide probe sets for diagnostic DNA microarrays," *Concurrency Computat.: Pract. Exper.* (2004) 16: 873-893.
Hyndman, D., et al., "Software to Determine Optimal Oligonucleotide Sequences Based on Hybridization Simulation Data," *BioTechniques* (1996) 20: 1090-1097.

*Primary Examiner*—Ram R. Shukla
*Assistant Examiner*—Anna Skibinsky
(74) *Attorney, Agent, or Firm*—Cantor Colburn LLP

(57) ABSTRACT

There is provided a method of designing a probe from a polynucleotide group comprising a plurality of polynucleotides, the method including: forming a polynucleotide group by selecting polynucleotides having a certain sequence; producing polynucleotide fragments having a certain length from each of the polynucleotides of the polynucleotide group and obtaining sequence and position information on the polynucleotide fragments; providing each polynucleotide fragment with a sequence specific identification number using the obtained sequence and position information of the polynucleotide fragments; and comparing the identification numbers of the fragments to select the probe.

6 Claims, 2 Drawing Sheets

METHOD OF DESIGNING PROBE FROM POLYNUCLEOTIDE GROUP COMPRISING PLURALITY OF POLYNUCLEOTIDES

CROSS-REFERENCE TO RELATED PATENT APPLICATION

This application claims the benefit of Korean Patent Application No. 10-2004-0085798, filed on Oct. 26, 2004, in the Korean Intellectual Property Office, the disclosure of which is incorporated herein in its entirety by reference.

BACKGROUND OF THE INVENTION

1. Field of the Invention

The present invention relates to a method of designing a probe from a polynucleotide group comprising a plurality of polynucleotides.

2. Description of the Related Art

A "probe" is a material that specifically binds to a target material. Two probe designing methods are generally used to design a nucleic acid probe according to whether the probe is a common probe or a specific probe.

A common probe is designed to find a common or consensus sequence among various species and family genes. The first step for designing a common probe is to find conserved genes. This is achieved by performing a keyword or homology search against a public-use database (e.g. GenBank and Medline) or performing homology analysis between one of the genes and whole database sequences. The second step is to retrieve all of the conserved genes. The third step is to perform a multiple alignment analysis using a commercially available program such as DNASIS (Hitachi Software of Brisbane, Calif.). In this step, a common polynucleotide among sequences is identified. Subsequently, a sequence of the obtained common polynucleotide is input into the program and the presence of a secondary structure is detected to select candidate probes having no secondary structure in a given Tm (melting temperature). The selected candidate probes are compared with whole sequences stored in a public-use database (e.g. Genbank) to determine the presence of a sequence causing cross hybridization, and a sequence that does not cause cross hybridization is selected as a final probe.

A specific probe is designed to find a unique sequence among various species, gene families and published sequences of a database. A specific probe hybridizes with one specific gene. The first step for selecting the probe is to find related genes, for example, by performing a keyword search on a public-use database (e.g. GenBank and Medline) and to obtain all information on the related genes. The second step is to find a common region and a unique region by performing a homology search on the obtained genes and the sequences published in a database (e.g. GenBank). Then, the obtained candidate probes are input into the program (such as DNASIS) and the presence of a secondary structure is determined to select probes having no secondary structure in a giver Tm (melting temperature). Finally, the obtained candidate probes are compared with sequences published in a database (e.g. GenBank) to determine the presence of an identical sequence, and a probe having no sequence identical to the published sequence is selected.

However, the above-described conventional methods involve a multiple alignment analysis. In the multiple alignment analysis, a plurality of target polynucleotides are aligned such that nucleotides correspond to each other under a specific condition and a probe is selected by comparing a completely matched region and with a mismatched region among the polynucleotides. However, since polynucleotides are aligned and their sequences are compared, the analysis takes a long time, and alignment accuracy of sequences may vary depending on alignment conditions. For example, the alignment accuracy may vary depending on a gap condition determining an allowed interval between nucleotides. Further, when a probe should be repeatedly designed, alignment of polynucleotides should be repeated.

In addition to these conventional methods, oligoprobe designation has been used to design a common probe or a specific probe (U.S. Pat. No. 5,556,749; Hitachi). Although this method involves the comparison of two sequences, it can be used to design a common probe or a specific probe if it is repeatedly applied to a plurality of sequences.

The Hitachi method involves the rapid comparison of two sequences A and B to identify whether the sequence A is identical to the sequence B but at least some number of base pairs. For example, whether a sequence identical to a sequence A having a total length of 20 bp or a sequence identical to all but 1 or 2 bp of the sequence A is present in a sequence B is rapidly found. In this method, a subsequence of the sequence A, which is called a "tuple", is produced and is compared with the sequence B. If a sequence identical to the subsequence is present in the sequence B, the bp of the subsequence are increased one by one until the length of the subsequence is the same as the total length of the sequence A. If a mismatch between A and B is greater than an allowed value (user's set value), it is concluded that the sequence A is not present in the sequence B on the basis of the allowed mismatch of bp. If the sequence A to be compared has 18 bp and the number of allowed mismatched bp is 2, a sequence completely identical to a subsequence of the sequence A having at least 6 bp should be present in the sequence B. Such a sequence is called a "k_tuple". The k_tuple is compared with the sequence B and if the type thereof is completely identical to a portion of the sequence B, the bp of the k_tuple are increased one by one.

Even though the above method involves the comparison of two sequences, it can be used to find a common sequence or a specific sequence by repeatedly performing such a comparison on a group of sequences having a certain length.

Nevertheless, there is still a demand for a method of rapidly and accurately designing a common probe or a specific probe from a plurality of polynucleotides.

SUMMARY OF THE INVENTION

The present invention provides a method of rapidly and accurately designing a probe.

According to an aspect of the present invention, there is provided a method of designing a probe from a polynucleotide group comprising a plurality of polynucleotides, the method comprising:

forming a polynucleotide group by selecting polynucleotides having a certain sequence;

producing polynucleotide fragments having a certain length from each of the polynucleotides of the polynucleotide group and obtaining sequence and position information on the polynucleotide fragments;

providing each polynucleotide fragment with a sequence specific identification number using the obtained sequence and position information of the polynucleotide fragments; and comparing the identification numbers of the fragments to select the probe.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
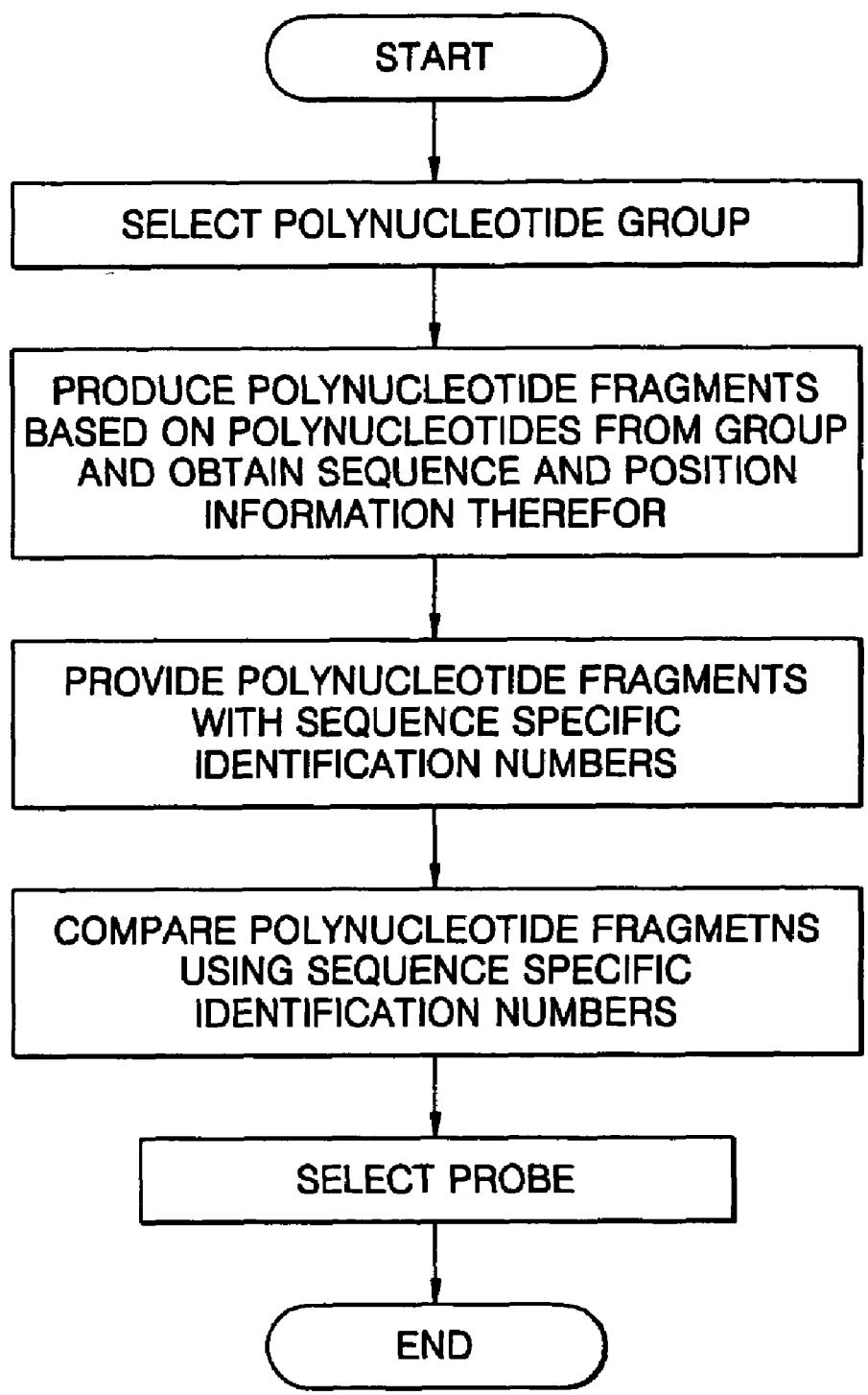
FIG. 1 is a flow chart illustrating a method according to an embodiment of the present invention.

A method of designing a probe from a plurality of polynucleotides according to an embodiment of the present invention includes: forming a polynucleotide group by selecting polynucleotides having a certain sequence; producing polynucleotide fragments having a certain length from each of the polynucleotides of the polynucleotide group and obtaining sequence and position information on the polynucleotide fragments; providing each polynucleotide fragment with a sequence specific identification number using the obtained sequence and position information of the polynucleotide fragments; and comparing the identification numbers of the fragments to select the probe.

In an embodiment of the method, the providing of the sequence specific identification number includes providing bases of nucleotides A, T, G and C with values of 0, $4^{(L-i)}/4$, $4^{(L-i)}/2$ and $4^{(L-i)} \times (3/4)$, respectively, where L is the length of each polynucleotide fragment and i sequentially increases from i=0 at a 5'-end nucleotide of the polynucleotide to i=L−1 at a 3'-end nucleotide of the polynucleotide fragment; combining the provided values; adding values from $4^1$ to $4^{(L-1)}$ to the sum; and providing the obtained value as the identification numbers of the polynucleotide fragment.

Herein, the term "probe" means a polynucleotide having a sequence that specifically binds to a target polynucleotide. Examples of probes include a common probe having a sequence specific to a plurality of polynuclebtides to binding to all of a plurality of polynucleotides and a specific probe having a sequence specific to only certain polynucleotides among a plurality of polynucleotides. A probe in this context can be used as primer for polynucleotide amplification. Even though the probe used in the present embodiment include mismatched nucleotides as well as completely complementary sequences, it includes a sequence that specifically binds to a target polynucleotide according to reaction conditions.

In an embodiment of the method, when a specific probe having mismatched nucleotides is selected, the providing the sequence specific identification number to each of the polynucleotide fragments includes producing polynucleotide fragments having at least one nucleotide mismatched to one of the polynucleotide fragments having a sequence specific identification number; and providing the produced polynucleotides with sequence specific identification numbers. In this case, the providing of a sequence specific identification number includes providing bases of nucleotides A, T, G and C with values of 0, $4^{(L-i)}/4$, $4^{(L-i)}/2$ and $4^{(L-i)} \times (3/4)$, respectively, where L is the length of each polynucleotide fragment and i sequentially increases from i=0 at a 5'-end nucleotide of the polynucleotide to i=L−1 at a 3'-end nucleotide of the polynucleotide fragment; combining the provided values; adding values from $4^1$ to $4^{(L-1)}$ to the sum; and providing the obtained value as the identification numbers of the polynucleotide fragment.

In the method, a first selected probe may be completely complementary to a target polynucleotide or have some mismatched nucleotides. When sequence specific probes having mismatched nucleotides are selected, it is necessary to select an optimum probe from these probes.

The method of the present embodiment may further include: obtaining sequence and position information of a polynucleotide fragment having a certain length produced from a sequence specific probe having mismatched nucleotides and providing the polynucleotide fragment with a sequence specific identification number using the sequence and position information; and comparing sequence specific identification numbers of the polynucleotide fragments obtained from the sequence specific probes having mismatched nucleotides to select a sequence specific probe having the sequence specific identification number that occurs with the most frequency.

In an embodiment of the method, a region in which probes specific to a target polynucleotide are frequently found is selected in a certain region using the position information of the polynucleotide fragment and the probes present in the region are selected as sequence specific probes.

FIG. 1 is a flow chart illustrating the method of the present embodiment. Referring to FIG. 1, first, a group of polynucleotides are selected. The polynucleotides include a target polynucleotide and other polynucleotides. The polynucleotides may be individual chromosomal polynucleotides or fragments derived therefrom.

Figure 2:
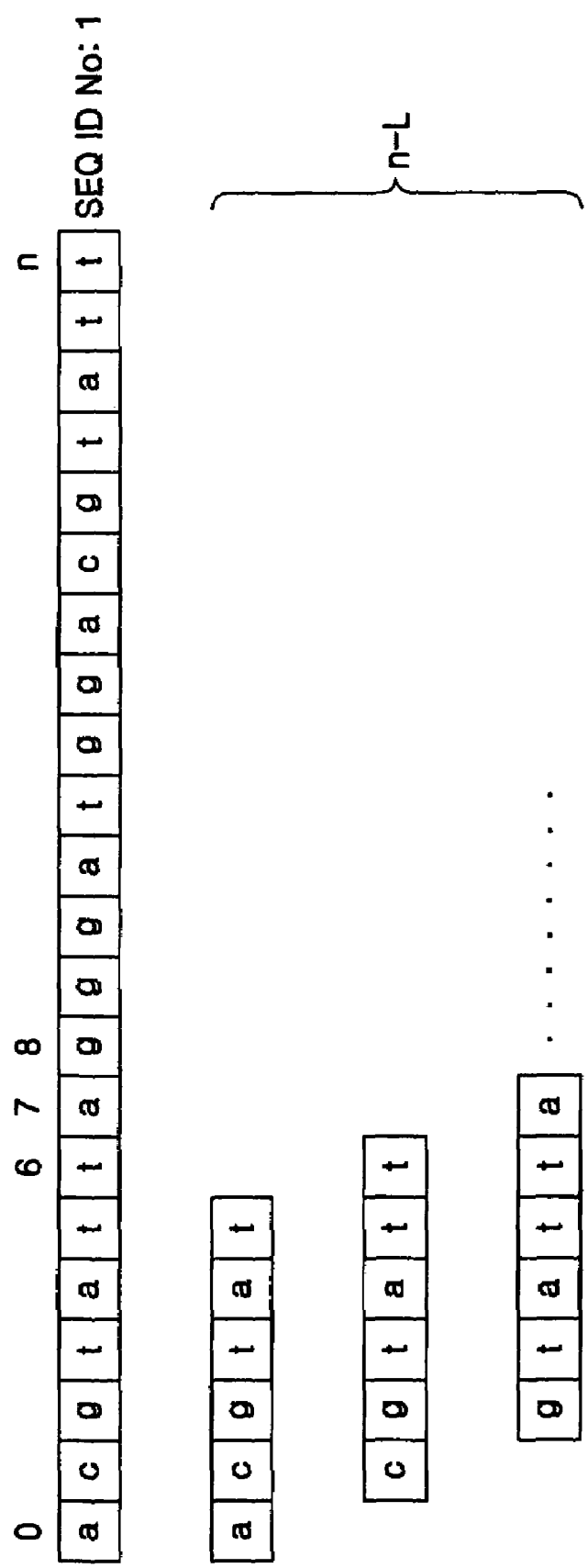
FIG. 2 illustrates the formation of 6 bp polynucleotide fragments from a 22 bp polynucleotide.

Then, polynucleotide fragments that have a certain length and can be used as probe candidates against the polynucleotides from the group of selected polynucleotides are produced. Sequence and position information of the produced polynucleotide fragments is obtained. The position information may be a position designated from a reference point (e.g., a replication initiating point) on a chromosome or a position designated from a 5'-end of a selected polynucleotide, but is not limited thereto. In the present embodiment, a method of producing the polynucleotide fragments from the group of selected polynucleotides is not particularly limited and may vary according to specific conditions for selecting a probe. For example, all possible fragments having a certain length can be produced. FIG. 2 illustrates an example of a method of producing L bp polynucleotide fragments from an n bp polynucleotide wherein L and n is 6 and 22, respectively. In FIG. 2, L bp polynucleotide fragments are produced while moving to the 3'-end of the polynucleotide at intervals of one nucleotide, wherein L is 6.

Then, the produced polynucleotide fragments are provided with sequence specific identification numbers. The identification numbers may be provided in any manner as long as they are unique to each of the fragments. For example, different numbers can be provided according to the position of the fragments from a 5'-end and the base sequence, and then the provided numbers are combined to obtain the identification number. Specifically, bases of nucleotides A, T, G and C are provided with values 0, $4^{(L-i)}/4$, $4^{(L-i)}/2$ and $4^{(L-i)} \times (3/4)$, respectively, where i=0 at a 5'-end nucleotide of a polynucleotide fragment and i=L−1 at a 3'-end nucleotide of a polynucleotide fragment, the obtained values are combined, the values from $4^1$ to $4^{(L-1)}$ are added to the sum, and the resulting value is provided as the identification number of the polynucleotide fragment. Examples of the sequence specific identification numbers provided to 8 bp fragments are as shown in Table 1.

TABLE 1

| Identification number | Sequence | Position |
|---|---|---|
| 31900 | agtctaga | 2174645 |
| 75750 | ctaggtag | 2771202 |
| 41027 | taggcgcc | 3800705 |

In the case of the fragment sequence: agtctaga, since L is 8 and i is 0 at a position of A at a 5'-end, the identification number therefor is obtained as follows: $\{0+4^7/2+4^6/4+4^5 \times 3/4+4^4/4+0+4^2/2+0\}+\{4+4^2+4^3+4^4+4^5+4^6+4^7\}=31900$.

Then, identification numbers of fragments obtained from a polynucleotide are compared with identification numbers of fragments obtained from another polynucleotide to select a probe from the fragments. Herein, comparison of "identification numbers of fragments" means a comparison of information (position, sequence, frequency) related to the identification numbers. For example, the frequency and position of fragments obtained from a polynucleotide can be compared, but the comparison is not limited thereto.

In this way, a fragment satisfying predetermined requirements can be selected as a probe. For example, fragments are produced from polynucleotides A, B and C and are provided with identification numbers; and the identification numbers are compared with each other to select a fragment derived from the polynucleotide A but not derived from polynucleotides B and C as a specific probe for the polynucleotide A.

Since the method of producing a specific or common probe of the present embodiment reuses an index obtained by once comparing sequences, it requires fewer comparing operations than a conventional method of performing a multiple sequence analysis to produce a specific or common probe or the Hitachi method (U.S. Pat. No. 5,556,749) in which a k_tuple seed sequence is produced and sequences are compared while increasing the bp of the seed sequence one by one. Even though the numbers of comparing operations performed in the present embodiment and in the Hitachi method may vary depending on the length of a common or specific sequence, the number of allowed mismatches, and the subject intended to extract a common or specific sequence thereof, they can be expressed by the following general equations.

The number of comparing operations of the present embodiment is in the range of $_{probeL}C_n < 0(n) < _{probeL}C_n \times$ dbSize, where probeL is a probe length, n is the number of allowed mismatches, dbSize is the number of sequences to be searched, and I is an average length of sequences to be searched.

The number of comparing operations of the Hitachi method is in the range of dbSize ((I−k_tupleL+I+n))<0(n) <dbSize (1−k_tupleL+I+probeL−k_tupleL+I), probeL is a probe length, and k_tupleL is a k_tuple length, n is the number of allowed mismatches, dbSize is the number of sequence to be searched, and I is an average length of sequences to be searched. The k_tuple length is the minimum length of a continuous sequence for a given probe length and number of mismatches. For example, if a mismatch of 2 bp is allowed for an 18 bp probe length, a continuous sequence of at least 6 bp is required.

The method of the present embodiment requires more comparisons than the Hitachi method. However, the Hitachi method requires time for loading sequences to memory, pre-treatment for a specific portion of a sequence to be analyzed, etc., whereas the method of the present embodiment does not require any time beyond the time for obtaining data since only an already-produced index is used. Considering that a processing time for sequence information is not required and the length of a real probe is about 20-30 bp, the number of comparing operations can be calculated in a practical time.

The method of the present embodiment includes producing candidate probes including mismatched nucleotides from candidate probes obtained according the above method and selecting a probe including a mismatched nucleotide from the produced candidate probes. For example, when a probe including a mismatched nucleotide for a polynucleotide of acgtat having an identification number of 141231 is selected, 3×n (n=the number of polynucleotides) polynucleotides having a mismatched nucleotide, for example, tcgtat, gcgtat, ccgtat, aagtat, atgtat, aggtat, etc., are obtained from the polynucleotide of acgtat, identification numbers are provided thereto as described above, and a probe can be selected by comparing identification numbers.

The method of the present embodiment can also be used to select a most appropriate probe from probes having nucleotides mismatched to a target polynucleotide. For example, fragments having a certain length are produced from a polynucleotide having a plurality of mismatched nucleotides, sequence specific identification numbers are provided to the produced fragments as described above, and a fragment having the highest frequency of a sequence completely complementary to a target polynucleotide can be selected as a probe by comparing identification numbers.

The method of the present embodiment can also be used to select a fragment displayed with a high frequency in a certain region as a probe. The selection of a probe is achieved by determining a certain sequence region using identification numbers and position information of polynucleotide fragments and comparing the frequency of identification numbers of fragments present in the limited region and identified as specific to a target polynucleotide.

EXAMPLES

In the present example, 8 bp probes specific to only E. coli O157:H7 were selected from chromosomal sequences of E. coli O157:H7 and E. coli K-12:MG1655. Further, a region in which 8 bp probes specific to only E. coli O157:H7 frequently appeared was selected and a probe in the region was selected.

First, a genome polynucleotide of E. coli O157:H7 (accession number AE005174: 5,498,450 bp) and a genome polynucleotide of E. coli K-12:MG1655 (accession number U00096: 4,639,221 bp) were selected, 8 bp fragments were produced from each of the polynucleotides, and sequence and position information of 8 bp fragments was obtained and stored using Oracle 9i database. A fragment specifically present in the genome polynucleotide of E. coli O157:H7 was selected by comparing the frequency of the obtained identification number for each fragment in the genome polynucleotide of E. coli O157:H7 and in the genome polynucleotide of E. coli K-12:MG1655.

As a result, 131 different 8 bp probes unique specific to the genome polynucleotide of E. coli O157:H7 were selected. It was determined that these probes were found at 320 sites. A polynucleotide appearing the most frequently in the genome polynucleotide of E. coli O157:H7 among the probes was a polynucleotide having a sequence: gtgggccc, and appeared 12 times. Some examples of the 131 probes specific to the genome polynucleotide of E. coli O157:H7 are provided in Table 2.

TABLE 2

| Identification number | Appearing frequency of E. coli O157:H7 in genome polynucleotide |
|---|---|
| 17566 | 6 |
| 25894 | 4 |
| 32550 | 1 |
| 32584 | 3 |
| 29309 | 2 |
| 29852 | 2 |
| 29855 | 7 |
| 30878 | 1 |
| 34972 | 2 |
| 35287 | 1 |
| 32926 | 1 |

Optimum probes were selected from the selected 131 different 8 bp probes. The selection of optimum probes was achieved by producing fragments having one mismatched bp for each probe and then comparing the frequency of polynucleotide sequences having the 1 mismatched bp in the genome polynucleotide of E. coli O157:H7 and in the genome polynucleotide of E. coli K-12:MG1655 and the number of different polynucleotide sequences having the 1 mismatched bp. Some of the results provided in Table 3.

According to the method of the present invention, the design of a probe can be rapidly and efficiently achieved even in the case of a very long polynucleotide such as a genome polynucleotide since the probe is selected using

TABLE 3

| Sequence of O157 specific probe | Identification number | Frequency of probes having 1 mismatched bp in genome nucleotide of K-12:MG1655 | Frequency of probes having 1 mismatched bp in genome nucleotide of O157:H7 | Number of different probes having 1 bp mismatched nucleotide in genome polynucleotide of K-12:MG1655 | Number of different probes having 1 mismatched bp in genome polynucleotide of O157:H7 | Ratio of frequency (O157:H7/ K12:MG1655) | Difference in the number of different probes (O157:H7 – K-12:MG1655) |
|---|---|---|---|---|---|---|---|
| gcctaggt | 70269 | 520 | 577 | 19 | 21 | 1.109 | 2 |
| gtctagct | 62081 | 533 | 584 | 24 | 24 | 1.096 | 0 |
| cggcctag | 82214 | 689 | 739 | 23 | 23 | 1.073 | 0 |
| aggcgccc | 33043 | 975 | 1201 | 24 | 24 | 1.232 | 0 |
| gactagaa | 57972 | 612 | 725 | 22 | 23 | 1.185 | 1 |
| accctagt | 38045 | 375 | 389 | 22 | 22 | 1.037 | 0 |
| cctctagg | 85150 | 227 | 273 | 21 | 24 | 1.203 | 3 |
| agcctagt | 33939 | 448 | 515 | 22 | 24 | 1.150 | 2 |
| aggtctag | 32550 | 415 | 465 | 21 | 22 | 1.121 | 1 |
| ctaggtcg | 75762 | 514 | 538 | 22 | 23 | 1.047 | 1 |
| cttcctag | 77094 | 548 | 637 | 22 | 23 | 1.162 | 1 |

As a result, a group of a sequence: cctctagg (85150) and probes having 1 mismatched bp to the sequence cctctagg was selected as an optimum group.

In the present Example, probes frequently appeared in a certain region among the selected probes were selected and an optimum probe was selected from the frequently appeared probes. When probes frequently appeared in a certain region, those probes can be used as a PCR primer for amplifying the region or as a probe in a hybridisation reaction for detecting a particular sequence. Further, a target polynucleotide obtained by an amplification reaction such as PCR could be analyzed using various probes. The extent to which probes appeared in a certain region was determined by simply determining the range of a region using position information and investigating the number of probes selected as described above, and included in the determined range.

It can be seen from the results that according to the method of an embodiment of present invention, polynucleotide fragments are obtained from a target polynucleotide, sequence specific identification numbers are provided thereto, and a probe can be designed using the same. Further, since identification numbers provided to polynucleotide fragments obtained from the target polynucleotide can be reused, a probe can be rapidly designed without aligning sequences each time as in the conventional method.

identification numbers. Further, design of a probe can be achieved without multiple alignment and separate cross hybridization assay processes since the probe is selected using identification numbers.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of designing a probe from a polynucleotide group comprising a plurality of polynucleotides, the method comprising:

providing a sequence for each polynucleotide in a plurality of polynucleotides;

forming a polynucleotide group consisting of all the sequences;

producing polynucleotide fragments having a certain length from each of the sequences of the polynucleotide group;

obtaining a sequence for each polynucleotide fragment;

providing, for each polynucleotide fragment, a sequence specific identification number using the sequence for the polynucleotide fragment;

comparing the sequence specific identification numbers of the polynucleotide fragments to each other to select a probe; and displaying the selected probe;

wherein the sequence specific identification number is calculated by providing bases of nucleotides A, T, G, and C in the sequence of the polynucleotide fragment with values of 0, $4^{(L-i)}/4$, $4^{(L-i)}/2$, and $4^{(L-i)} \times (3/4)$, respectively, where L is the length of the polynucleotide fragment and i sequentially increases from i=0 at a 5'-end nucleotide of the polynucleotide to i=L−1 at a 3'-end nucleotide of the polynucleotide fragment;

adding the provided values for each base in the sequence and values from $4^1$ to obtain a sum; and providing the sum as the sequence specific identification number of the polynucleotide fragment.

2. The method of claim 1, wherein the probe is a specific probe or a common probe.

3. The method of claim 1, wherein, if the selected probe is a specific probe comprising mismatched nucleotides, the method further comprises:

producing polynucleotide fragments having at least one nucleotide mismatched to one of the polynucleotide fragments having a sequence specific identification number; and providing the mismatched polynucleotide fragments with sequence specific identification numbers.

4. The method of claim 3, wherein providing a mismatched polynucleotide fragment with a sequence specific identification number comprises:

providing bases of nucleotides A, T, G and C in a sequence of the mismatched polynucleotide fragment with values of 0, $4^{(L-i)}/4$, $4^{(L-i)}/2$ and $4^{(L-i)} \times (3/4)$, respectively, where L is the length of the mismatched polynucleotide fragment and i sequentially increases from i=0 at a 5'-end nucledotide of the mismatched polynucleotide fragment to i=L−1 at a 3'-end nucleotide of the mismatched polynucleotide fragment;

adding the provided values for the sequence of the mismatched polynucleotide fragment and values from $4^1$ to $4^{(L-1)}$ to obtain a sum; and providing the sum as the sequence specific identification number of the mismatched polynucleotide fragment.

5. The method of claim 3, further comprising:

producing polynucleotide fragments comprising mismatched nucleotide and having a certain length from the selected specific probe;

obtaining a sequence for each of the produced polynucleotide fragments;

providing each of the produced polynucleotide fragments with sequence specific identification numbers based on the sequence; and comparing the sequence specific identification numbers of the produced polynucleotide fragments obtained from each of the selected specific probes; and selecting the most frequently appearing specific probe comprising a mismatched nucleotide.

6. The method of claim 1, further comprising selecting a region of a polynucleotide in which a probe specific to the polynucleotide appears frequently using position information of the polynucleotide fragments, and probes present in the region are selected as sequence specific probes.

* * * * *

SEQUENCE LISTING

```
<160> NUMBER OF SEQ ID NOS: 1

<210> SEQ ID NO 1
<211> LENGTH: 22
<212> TYPE: DNA
<213> ORGANISM: artificial
<220> FEATURE:
<223> OTHER INFORMATION: Hypothetical sequence

<400> SEQUENCE: 1
acgtattagg gatggacgta tt                                              22
```